United States Patent [19]

Baer et al.

[11] Patent Number: 4,464,307

[45] Date of Patent: Aug. 7, 1984

[54] SUBSTITUTED ACID CHLORIDE PROCESS

[75] Inventors: Ted A. Baer, Palo Alto; Scott G. Broadbent, Milpitas, both of Calif.

[73] Assignee: Zoecon Corporation, Palo Alto, Calif.

[21] Appl. No.: 439,738

[22] Filed: Nov. 8, 1982

[51] Int. Cl.$^3$ ............................................. C07C 51/60
[52] U.S. Cl. ................................................. 260/544 N
[58] Field of Search ..................................... 260/544 N

[56] References Cited

U.S. PATENT DOCUMENTS 3,925,418 12/1975 Williams et al. ................ 260/544 D

OTHER PUBLICATIONS

Babad, Harry et al., "The Chemistry of Phosgene" *Chemical Reviews* vol. 73 (1973) pp. 75–91.

*Primary Examiner*—Natalie Trousof
*Assistant Examiner*—L. Hendriksen
*Attorney, Agent, or Firm*—William B. Walker; Donald W. Erickson; Jacqueline Larson

[57] ABSTRACT

The acid chlorides of N-substituted-2-aminocarboxylic acids are prepared by treating the carboxylic acids with phosgene in the presence of a catalytically effective amount of a water soluble tertiary amine, which acid chlorides are useful in the manufacture of insecticides.

5 Claims, No Drawings

SUBSTITUTED ACID CHLORIDE PROCESS

BACKGROUND OF THE INVENTION

1. Field of the Invention

This invention relates to the preparation of substituted acid chlorides which are useful as intermediates for preparing pesticidally active compounds. In the novel process of this invention, excellent yields of pure substituted amino acid chlorides in a hydrocarbon solvent are obtained from the corresponding substituted amino acids.

2. Description of the Prior Art

U.S. Pat. No. 4,243,819 to Henrick et al describes substituted amino acid compounds suitable for use in the process of this invention. It also describes the use of the corresponding substituted amino acid chlorides as intermediates for preparing pesticidally active esters.

The chemical reaction of a carboxylic acid with phosgene in the presence of a tertiary amide to yield the corresponding acid chloride is a well known reaction. The use of N-methyl-2-pyrrolidone in the general reaction of organic acids to yield chlorides has been described in *M-PYROL N-Methyl-2-Pyrrolidone Handbook*, GAF Corporation (1972). More specific reaction details have been disclosed in other publications. Babad et al, *Chemical Reviews* Vol. 73 No. 1, 81-82 (1973); Ulrich et al, *J.Org.Chem.* 32 4052 (1967); German Pat. No. 1,167,819 (1964); German OLS No. 1,931,074 (1968) and British Pat. No. 1,159,266 (1969) describe the reaction of carboxylic acids or anhydrides with phosgene using a number of catalysts including tertiary amides to yield the corresponding acid chlorides. All of these references teach reaction temperatures approaching 100° C. during an initial stage, and thereafter, increasing temperatures up to the reflex temperature (115° to 150° C.). In a final step, the solvent is removed by distillation at temperatures substantially above 100° C. Elevated temperatures are required and minimal catalytic amounts of tertiary amides are used.

The prior art processes do not produce amino acid chlorides in high yield because the end products are unstable at high temperatures.

SUMMARY OF THE INVENTION

In summary, this invention is a process for preparing substituted amino acid chlorides from the corresponding acids in high yield. The invention is a process for preparing a compound of Formula (I):

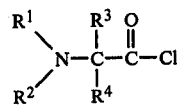
(I)

wherein
$R^1$ is cycloalkyl, cycloalkenyl, cycloalkenyl substituted with halo or lower alkyl, or the group

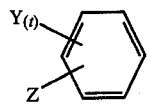

in which t is zero, one, two, three or four; Y is independently selected from the group consisting of hydrogen, lower alkyl, lower haloalkyl, lower alkoxy, lower alkythio, lower alkylcarbonyl, lower alkoxycarbonyl, lower aryloxy, halogen, cyano, nitro, or lower haloalkythio; and Z is independently selected form the values of Y, cycloalkyl and lower haloalkoxy; or Y and Z together form a methylenedioxy group;

$R^2$ is hydrogen, lower alkyl, lower haloalkylcarbonyl, or formyl;

$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms; and $R^4$ is hydrogen or fluoro, comprising the steps of:

(a) reacting a compound of Formula II

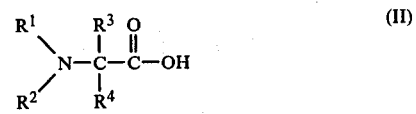
(II)

wherein $R^1$, $R^2$, $R^3$ and $R^4$ are as defined above, with phosgene in the presence of a catalytically effective amount of a water-soluble tertiary amide at a temperature of from $-10°$ C. to $+10°$ C. in an aliphatic or aromatic hydrocarbon solvent having a boiling point of from 35° to 140° C. until compound of Formula (I) is formed in the reaction mixture; and (b) extracting the reaction mixture with water at a temperature of from $-10°$ C. to $+10°$ C. to remove the catalyst, unreacted phosgene, by-product hydrogen chloride and any other water-soluble impurities.

DETAILED DESCRIPTION OF THE INVENTION

The prior art processes require heating at elevated temperatures to drive the reaction and purify the product. However, the amino acid chlorides are unstable at the process temperatures of the prior art. At the low temperatures of the process of this invention, preferably with two equivalents of N-methylpyrrolidone and using an aqueous extraction for purification to remove unreacted phosgene, catalyst and by-products, a high yield of amino acid chloride is obtained.

In general, the process of this invention comprises reacting the compound of Formula (II) with phosgene in a hydrocarbon solvent in the presence of a tertiary amide catalyst to yield the compound of Formula (I). For example, 2-N-(2-chloro-4-trifluoromethylphenyl)amino-3-methylbutyroyl chloride can be prepared from the corresponding 2-N-(2-chloro-4-trifluoromethylphenyl)amino-3-methylbutyric acid. The concentration of the reactant of Formula (II) in the reaction mixture can be from 10 to 30 weight percent and is preferably at the upper end of this range.

The solvents suitable for use in the process of this invention are, in general, aliphatic and aromatic hydrocarbons or mixtures thereof. Suitable hydrocarbon solvents have atmospheric boiling points of 35°–140° C. The preferred solvents are aliphatic hydrocarbons having boiling points of from 35°–140° C. and optimally from 35°–100° C. Examples of preferred solvents are straight and branch-chained pentanes, hexanes and mixtures thereof.

Water-soluble tertiary amides are essentially catalysts in the process of this invention. Suitable tertiary amides include N-formylpiperidine, dimethylformamide, dimethylacetamide and N-methyl-2-pyrrolidone. The preferred tertiary amide catalyst is N-methyl-2-pyrrolidone. A catalytically effective amount of tertiary amide is used in the reaction mixture. This is generally at least two molecular equivalents.

The reactant of Formula (II) and the tertiary amide are mixed in the reaction solvent prior to the addition of phosgene. While the reaction mixture is maintained at a temperature within the critical range of from −10° to +10° C., the phosgene is slowly added until compound of Formula (I) is formed in the reaction mixture. Generally from 30 minutes to one hour is required for completing the reaction.

When the reaction is completed, the reaction mixture is extracted with water while maintaining a low temperature. During the extraction, it is preferred that the overall mixture be maintained at a temperature of from 10° C. or less. The reaction mixture is mixed with sufficient water to extract the impurities. During this step, unreacted phosgene, catalyst and hydrochloric acid are removed.

The prior art processes for preparing acid chlorides from the corresponding carboxylic acids by reaction with phosgene have required a high temperature which are not suitable for preparing acid chlorides from the compounds of Formula (II) in high yield. At the elevated temperatures, low yields of the compound of Formula I are obtained owing to decomposition. Purification by distillation required in the prior art processes is completely useless for the same reason.

In the process of this invention, a very high yield of product of Formula (I) is obtained. Critical to the process of this invention are the low reaction temperatures and low purification temperatures. Surprisingly, even though organic acid chlorides are generally known to be reactive with water, the water extraction can be carried out with a minimum of end product loss if the extraction mixture temperature is maintained at or below +10° C.

The product compounds for Formula (I) are obtained described in the hydrocarbon solvent, and this solution can be used directly in subsequent reactions to prepare end products. Esterification of the products of Formula (I) with organic alcohols to yield pesticidally active esters is described in U.S. Pat. No. 4,243,819.

The processes of this invention are further illustrated by the following specific, but non-limiting examples. Unless otherwise specified, the examples described hereinafter represent actual experiments. All temperatures are given as degrees centigrade and all percents as percents by weight unless otherwise specified.

EXAMPLE 1

A mixture of 100.0 g of 2-N-(2-chloro-4-trifluoromethylphenyl)amino-3-methylbutyric acid, 67.1 g of N-methylpyrrolidone and 222 g of hexane was added to a one l 4-neck flask equiped with a magnetic stirrer. The contents were cooled to 0° C., and 43.2 g of phosgene was added as a gas while maintaining the reaction temperature of 0° C. When the reaction was complete, the reaction mixture was cooled to −5° C. and water was added. The temperature rose to +10° C. After separating the aqueous phase was removed. A hexane solution of (R)-2-N-(2-chloro-4-trifluoromethylphenyl)amino-3-methylbutyroyl chloride was obtained. The final acid chloride analysis by gas chromatography showed a conversion to acid chloride of 96.1%.

EXAMPLE 2

(R)-2-N-(2-chloro-4-trifluoromethylphenyl)amino-3-methylbutyric acid (200.0 g, 0.677 mol), N-methylpyrrolidone (134.2 g, 1.354 mol) and hexane (482 g) were combined, followed by addition of phosgene (88.0 g, 0.89 mol) at −8°. The reaction mixture was washed twice with 125 ml of water. The aqueous phase was removed, yielding (R)-2-N-(2-chloro-4-trifluoromethylphenyl)amino-3-methylbutyroyl chloride in hexane. Analysis by gas chromatography showed a product purity of 95.5%.

EXAMPLE 3

A mixture of 20.49 lbs of (R)-2-N-(2-chloro-4-trifluoromethylphenyl)amino-3-methylbutyric acid, 13.75 lbs of N-methylpyrrolidone and 92.2 lbs of hexane was cooled to −8° with stirring under nitrogen atmosphere. To this cooled mixture was slowly added 9.85 lbs of phosgene gas while the temperature was maintained at −8°. One pound aliquots of the phosgene were added approximately every 5 to 10 minutes. The mixture was then extracted with 24.6 lbs of water while maintaining the temperature at −8° C., yielding a hexane solution of (R)-2-N-(2-chloro-4-trifluoromethylphenyl)amino-3-methylbutyroyl) chloride. Analysis of the reaction mixture showed 97.2% acid chloride.

EXAMPLE 4

A mixture of 40.0 g (135.4 mmol) of 2-N-(2-chloro-4-trifluoromethylphenyl)amino-3-methylbutyric acid, 26.8 g (270.7 mmol) of N-methylpyrrolidone and 180.0 g of hexane was cooled to −8° with stirring under nitrogen atmosphere. To this cooled mixture was slowly added 20.1 g (203.0 mmol) of phosgene gas, delivered subsurfacely, with temperature maintained at −8° until the reaction was complete as determined by GLC analysis. The reaction mixture was then rapidly poured into 50 ml of water containing 7.0 g of sodium chloride, with the temperature maintained at −8°. The resulting two-phase system was stirred briefly, and the phases were allowd to separate. The aqueous phase was removed, leaving 2-N-(2-chloro-4-trifluoromethylphenyl)amino-3-methylbutyroyl chloride in hexane solution. Gas chromatography showed 95.8% acid chloride.

EXAMPLE 5

(Hypothetical) Repeating the procedure of Example 1 but replacing 2-N-(2-chloro-4-trifluoromethylphenyl)amino-3-methylbutyric acid with an equivalent amount of the compounds under Column I yields the respective acid chloride under Column II.

I

2-N-(3,4,5-trimethoxyphenyl)amino-3-methylbutyric acid
2-N-(4-ethoxyphenyl)amino-3-methylbutyric acid
2-N-(2,4-dimethoxyphenyl)amino-3-methylbutyric acid
2-N-(3,5-dimethoxyphenyl)amino-3-methylbutyric acid
2-N-(2-methoxyphenyl)amino-3-methylbutyric acid
2-N-(4-ethylphenyl)amino-3-methylbutyric acid
2-N-(2,4,6-trimethylphenyl)amino-3-methylbutyric acid
2-N-(4-nitrophenyl)amino-3-methylbutyric acid
2-N-(2,4,6-trichlorophenyl)amino-3-methylbutyric acid
2-N-(4-fluorophenyl)amino-3-methylbutyric acid 2-N-(4-bromophenyl)amino-3-methylbutyric acid
2-N-(3-chloro-2-methoxyphenyl)amino-3-methylbutyric acid
2-N-(2-chloro-4-methylphenyl)amino-3-methylbutyric acid
2-N-(2,6-dichlorophenyl)amino-3-methylbutyric acid
2-N-(4chloro-2-nitrophenyl)amino-3-methylbutyric acid
2-N-(2,6-dichloro-4-nitrophenyl)amino-3-methylbutyric acid
2-N-(4-methylcarbonylphenyl)amino-3-methylbutyric acid
2-N-(3-cyanophenyl)amino-3-methylbutyric acid
2-N-(2,6-dimethylphenyl)amino-3-methylbutyric acid
2-N-(2,5-dimethylphenyl)amino-3-methylbutyric acid
2-N-(2-fluoro-4-trifluoromethylphenyl)amino-3-methylbutyric acid
2-N-(4-chlorophenyl)amino-3-methylbutyric acid
2-N-(4-chloro-2-fluorophenyl)amino-3-methylbutyric acid
2-N-(3-fluoro-4-methylphenyl)amino-3-methylbutyric acid
2-N-(2-fluoro-4-methylphenyl)amino-3-methylbutyric acid
2-N-(4-bromo-2-fluorophenyl)amino-3-methylbutyric acid

II

2-N-(3,4,5-trimethoxyphenyl)amino-3-methylbutyroyl chloride
2-N-(4-ethoxyphenyl)amino-3-methylbutyroyl chloride
2-N-(2,4-dimethoxyphenyl)amino-3-methylbutyroyl chloride
2-N-(3,5-dimethoxyphenyl)amino-3-methylbutyroyl chloride
2-N-(2-methoxyphenyl)amino-3-methylbutyroyl chloride
2-N-(4-ethylphenyl)amino-3-methylbutyroyl chloride
2-N-(2,4,6-trimethylphenyl)amino-3-methylbutyroyl chloride
2-N-(4-nitrophenyl)amino-3-methylbutyroyl chloride
2-N-(2,4,6-trichlorophenyl)amino-3-methylbutyroyl chloride
2-N-(4-fluorophenyl)amino-3-methylbutyroyl chloride
2-N-(4-bromophenyl)amino-3-methylbutyroyl chloride
2-N-(3-chloro-2-methoxyphenyl)amino-3-methylbutyroyl chloride
2-N-(2-chloro-4-methylphenyl)amino-3-methylbutyroyl chloride
2-N-(2,6-dichlorophenyl)amino-3-methylbutyroyl chloride
2-N-(4-chloro-2-nitrophenyl)amino-3-methylbutyroyl chloride
2-N-(2,6-dichloro-4-nitrophenyl)amino-3-methylbutyroyl chloride
2-N-(4-methylcarbonylphenyl)amino-3-methylbutyroyl chloride
2-N-(3-cyanophenyl)amino-3-methylbutyroyl chloride
2-N-(2,6-dimethylphenyl)amino-3-methylbutyroyl chloride
2-N-(2,5-dimethylphenyl)amino-3-methylbutyroyl chloride
2-N-(2-fluoro-4-trifluoromethylphenyl)amino-3-methylbutyroyl chloride
2-N-(4-chlorophenyl)amino-3-methylbutyroyl chloride
2-N-(4-chloro-2-fluorophenyl)amino-3-methylbutyroyl chloride
2-N-(3-fluoro-4-methylphenyl)amino-3-methylbutyroyl chloride
2-N-(2-fluoro-4-methylphenyl)amino-3-methylbutyroyl chloride
2-N-(4-bromo-2-fluorophenyl)amino-3-methylbutyroyl chloride

The invention claimed is:

1. A process for preparing 2-N-(2-chloro-4-trifluoromethylphenyl)amino-3-methylbutyroyl chloride comprising the steps of:
   (a) reacting 2-N-(2-chloro-4-trifluoromethylphenyl)amino-3-methylbutyric acid with phosgene in the presence of a catalytically effective amount of a water-soluble tertiary amide in an aliphatic or aromatic hydrocarbon solvent having a boiling point of from 35° to 140° C. at a temperature of from −10° to +10° C. until 2-N-(2-chloro-4-trifluoromethylphenyl)amino-3-methylbutyroyl chloride is formed in the reaction mixture; and
   (b) extracting the reaction mixture with water at a temperature of from −10° C. to +10° C. to remove impurities.

2. The process of claim 1 wherein the solvent is an aliphatic hydrocarbon.

3. The process of claim 2 wherein the solvent has a boiling point in the range of from 35° to 100° C.

4. The process of claim 2 wherein the tertiary amide is selected from the group consisting of N-methylpyrrolidone, dimethylformamide, dimethylacetamide, and N-formylpiperidine.

5. The process of claim 4 wherein the solvent has a boiling point in the range of from 35° to 100° C.

* * * * *